US006552348B2

(12) United States Patent
Cherry et al.

(10) Patent No.: US 6,552,348 B2
(45) Date of Patent: Apr. 22, 2003

(54) APPARATUS AND METHOD FOR BREAST CANCER IMAGING

(75) Inventors: Simon R. Cherry, Los Angeles, CA (US); Johannes Czernin, Pacific Palisades, CA (US); Niraj K. Doshi, Rosemead, CA (US); Yiping Shao, North Hollywood, CA (US); Robert W. Silverman, Sherman Oaks, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/737,119

(22) Filed: Dec. 14, 2000

(65) Prior Publication Data

US 2001/0040219 A1 Nov. 15, 2001

Related U.S. Application Data

(60) Provisional application No. 60/170,746, filed on Dec. 14, 1999.

(51) Int. Cl.[7] .............................................. G01T 1/164
(52) U.S. Cl. ......................... 250/363.03; 250/363.02; 250/363.04
(58) Field of Search ...................... 250/363.01, 363.02, 250/363.03, 363.04

(56) References Cited

U.S. PATENT DOCUMENTS 4,879,464 A * 11/1989 Iinuma ................... 250/363.02
5,753,917 A * 5/1998 Engdahl ................. 250/363.02

OTHER PUBLICATIONS

Thompson, C.J. et al., "Positron Emission Mammography (PEM): A Promising Technique for Detecting Breast Cancer," IEEE Transactions on Nuclear Science 42(4):1012–1017 (1995).

Thompson, C.J. et al., "Feasibility study for positron emission mammography," Medical Physics 21(4):529–537 (1994).

Robar, J.L. et al., "Construction and calibration of detectors for high–resolution metabolic breast cancer imaging," Nuclear Instruments and Methods in Physics Research A 329:402–406 (1997).

Weinberg, I. et al., "Preliminary results for positron emission mammography: real–time functional breast imaging in a conventional mammography gantry," European Journal of Nuclear Medicine 23(7):804–806 (1996).

Freifelder, Richard et al., "Dedicated PET scanners for breast imaging," Phys. Med. Biol. 42:2463–2480 (1997).

Hutchins, G.D. et al., "Evaluation of Prototype Geometries for Breast Imaging with Pet Radiopharmaceuticals," The Journal of Nuclear medicine, Scientific Papers, Proceedings of the 42nd Annual Meeting 36(5):69P–70P (1995).

Moses, W.W. et al., "PET Camera Designs for Imaging Breast Cancer and Axillary Node Involvement," The Journal of Nuclear Medicine, Scientific Papers, Proceedings of the 42nd Annual Meeting 36(5):69P (1995).

Berman, A.M. et al., "Technique to obtain positron emission mammography images in registration with x–ray mamograms," Med. Phys. 25(11):2119–2129 (1998).

(List continued on next page.)

Primary Examiner—Constantine Hannaher
Assistant Examiner—Albert Gagliardi
(74) Attorney, Agent, or Firm—Fulbright & Jaworski L.L.P.

(57) ABSTRACT

A detector for use in a dedicated PET scanner for cancer applications, particularly breast cancer applications, using a LSO scintillator, a lightguide coupling arrangement, and an efficient way to construct the scintillator array, which provides a flexible imaging system for breast cancer applications with high sensitivity and high spatial resolution in a compact, cost effective, design.

9 Claims, 14 Drawing Sheets

OTHER PUBLICATIONS

Williams, M.B. et al., "Gamma ray detectors for breast imaging," *SPIE* 3115:226–234 (1997).

Casey, M.E. et al., "A Multicrystal Two Dimensional BGO Detector Systemd for Positron Emission Tomography," *IEEE Transactions on Nuclear Science* 33(1):460–463 (1986).

Cherry, S.R. et al., "A Comparison of PET Detector Modules Employing Rectangular and Round Photomultiplier Tubes," *IEEE Transactions on Nuclear Science* 42(4):1064–1068 (1995).

Vaquero, J.J. et al., "Performance Characteristics of a Compact Positron–Sensitive LSO Detector Module," *IEEE Transactions Onmedical Imaging* 17(6):967–978 (1998).

Pani, R. et al., "Multi–PSPMT Scintillation Camera," *IEEE Transactions on Nuclear Science* 46(3):702–708 (1999).

Slates, R. et al., "Chemical Polishing of LSO Crystals to Increase Light Output," *IEEE Transactions on Nuclear Science* 47(3):1018–1023 (2000).

Huber, J.S. et al., "Geometry and surface treatment dependence of the light collection from LSO crystals," *Nuclear Instruments and Methods in Physics Research A* 437:374–380 (1999).

Kurashige, K. et al., "Surface Polishing of GSO cintillator Using Chemical Process," *IEEE Transactions on Nuclear Science* 45(3):522–524 (1998).

Raylman, R.R. et al., "The potential role of positron emission mamography for detection of breast cancer. A phantom study," *Med. Phys.* 27(8):1943–1954 (2000).

\* cited by examiner

FIG. 6
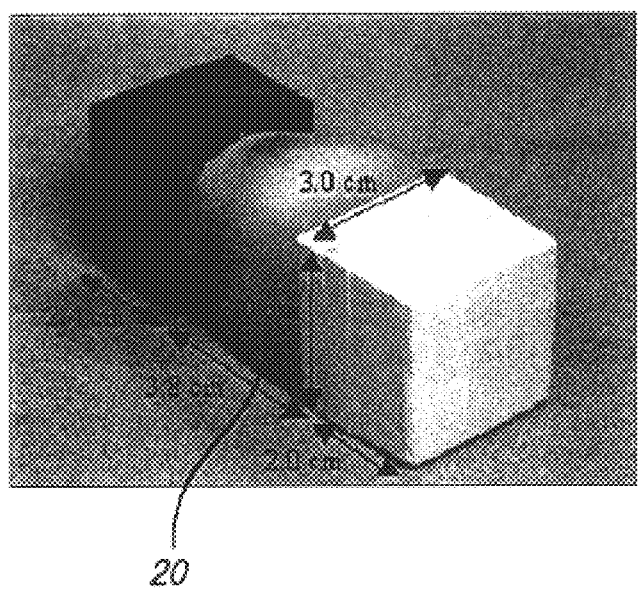
20
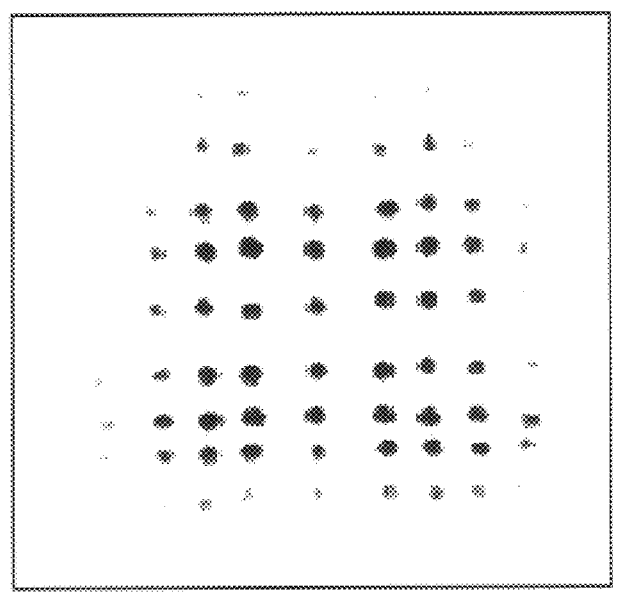
FIG. 7

FIG. 11
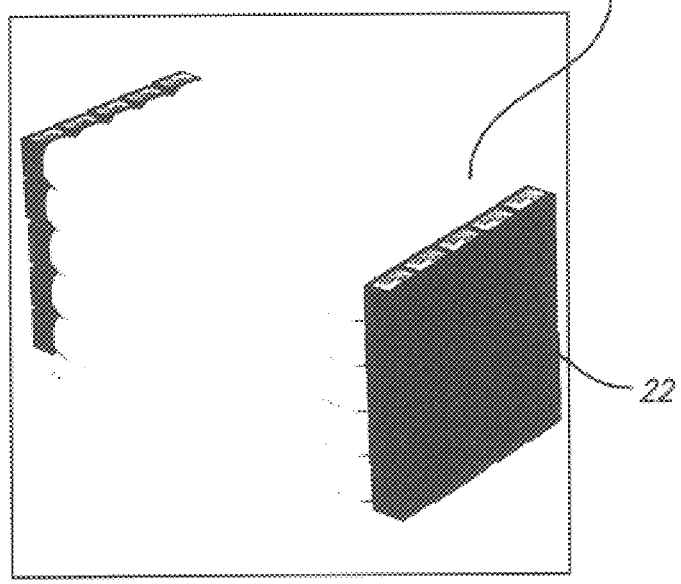
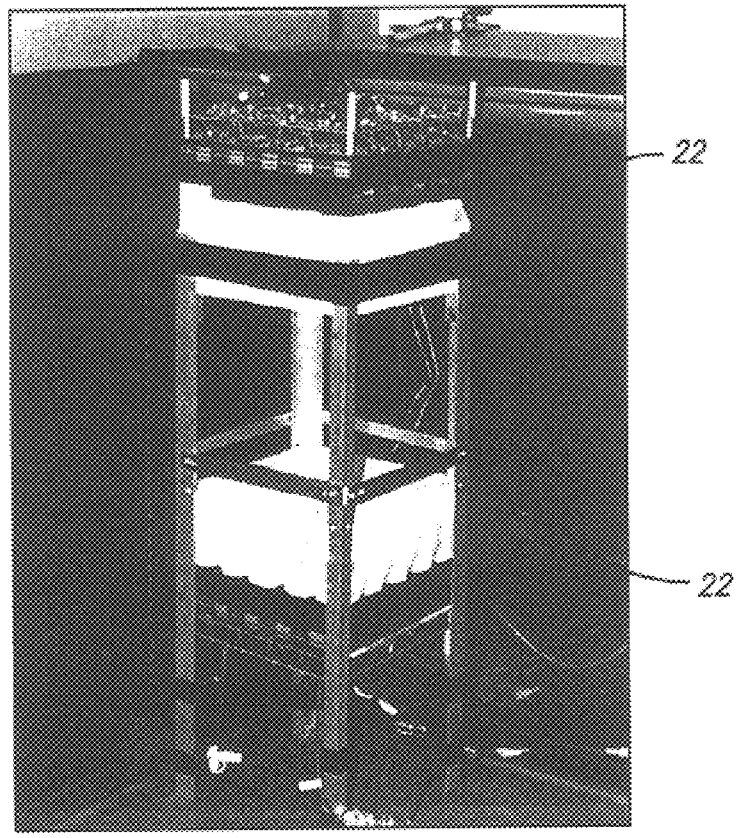
FIG. 12

APPARATUS AND METHOD FOR BREAST CANCER IMAGING

CROSS-REFERENCE WITH RELATED APPLICATIONS

This application claims the benefit of U.S. Provisional Application No. 60/170,746, filed Dec. 14, 1999, which is herein incorporated by reference.

STATEMENT REGARDING FEDERALLY SPONSORED RESEARCH OR DEVELOPMENT

This invention was made with Government support under Grant No. DAMD17-96-1-6200, awarded by the U.S. Department of the Army. The Government has certain rights in this invention.

BACKGROUND OF THE INVENTION

1. Field of the Invention

This invention relates generally to an apparatus and method for medical examination, in particular, a lutetium oxyorthosilicate (LSO) or light-output equivalent positron emitting tomography (PET) detector.

2. Description of Related Art

The American Cancer Society has predicted that there will be more than 181,000 new breast cancer cases and more than 40,000 deaths from breast cancer in the United States in 2000. [American Cancer Society, "Cancer Facts and Figures—1999," American Cancer Society, Atlanta, Ga. (1999).] Breast cancer is also the second leading cause of cancer death in women. Currently, mammography and physical breast examination, provide the two most effective methods for screening potential breast cancer patients. Although mammography allows the detection of very small, non-palpable lesions, it has a limited diagnostic accuracy for detecting cancer and image interpretation is subject to considerable inter-observer and intra-observer variability. The incidence of positive biopsies performed after mammographic findings ranges from 9% to 65%, with most investigators reporting a 15 to 30% positive biopsy rate. The sensitivity of detection by mammography drops considerably in women with dense, fibrocystic breasts.

Microcalcifications, one of the classic signs of occult malignancies, have a low predictive value of only 11.5% for the presence of cancer. The predictive value of masses that are thought to definitely represent malignancies is about 74%, but masses thought to be possibly malignant turn out to be carcinoma in only 5.4% of the cases. [M. Moskovitz, "The predictive value of certain mammographic signs in screening for breast cancer," Cancer, 51, 1007–1011 (1983)]. Also, several studies have reported substantial variability among radiologists in interpretation of mammographic examinations. [K. Kerlikowske, et al., "Variability and accuracy in mammographic interpretation using the American College of Radiology Breast Imaging Reporting and Data System," J. Natl. Can. inst., 90, 1801–1809 (1998)]. Therefore, mammography is a useful screening tool for detecting cancer, but it is limited by a large number of false positive tests, which result in unnecessary biopsies. Mammography is also limited by a considerable number of false negative tests, which result in the missed diagnosis of cancer.

It is also possible to use radio-pharmaceutical and radionuclide imaging to detect cancers, such as [$^{18}$F]fluoro-2-deoxy-D-glucose (FDG). FDG is a radioactive analog of glucose, which is phosphorylated and trapped within cells. After a patient receives a dose of FDG, she may be examined with a detector that senses the gamma rays produced by $^{18}$F. Positron emission tomography (PET), using FDG as a tracer of tumor glucose metabolic activity, is an accurate non-invasive imaging technology which probes tissue and organ function rather than structure. [See U.S. Pat. No. 5,453,623 and U.S. Pat. No. 5,961,457]. The increased rate of glycolysis in neoplastic cells, independent of the oxygen concentration present, has been previously reported. [O. Warburg, "On the origins of cancer cells," Science, Vol. 123, 309–314 (1956) and U.S. Pat. No. 5,969,358]. This information is fundamental to the utility of FDG for imaging human neoplasms.

Whole body PET scanners are used clinically to diagnose and to stage a wide variety of cancers. [C. K. Hoh, et al., "PET in oncology: will it replace the other modalities?" Sem. Nucl. Med., 27, 94–106 (1997)]. PET scanners detect breast cancer with sensitivities between 70 and 90% and with specificities of 84–97%. [N. Y. Tse, et al., "The application of Positron Emission Tomographic imaging with fluorodeoxyglucose to the evaluation of breast disease," Ann Surg., 216, 27–34 (1992); O. E. Nieweg, et al., "Positron Emission Tomography of Glucose Metabolism in Breast Cancer: Potential for Tumor Detection, Staging, and Evaluation of Chemotherapy," Ann. N. Y. A. Sci., 698, 423–448 (1993); and R. L. Wahl, et al., "Primary and Metastatic Breast Carcinoma: Initial Clinical Evaluation with PET with the Radiolabeled Glucose Analogue 2-[F-18]-Fluoro-2-deoxy-D-glucose," Radiology, 179, 765–770 (1991)]. A high diagnostic accuracy of PET imaging for staging of axillary lymph node involvement has also been reported. [L. Adler, et al., "Axillary lymph node metastases: screening with F-18 2-deoxy-2fluoro-D-glucose (FDG) PET," Radiology, 203, 323–327 (1997)]. The lower than desired diagnostic accuracy reported for PET imaging is due to relatively poor accuracy for detecting tumors of less than 1 cm in size. [N. Avril, et al., "Metabolic characterization of breast tumors with positron emission tomography using F-18 fluorodeoxyglucose," J Clin. Onc., 14, 1848–1857 (1996)].

Most PET imaging technology is currently based on scintillation detectors. Radiation detection begins by injecting isotopes with short half-lives into a patient's body. The isotopes are absorbed by target areas within the body, causing the isotope to emit positrons that are detected when they generate gamma rays. When in the human body, the positrons collide with electrons and the two annihilate each other, releasing gamma rays. The emitted rays move in opposite directions, leave the body and strke the array of radiation detectors. In the majority of commercial PET systems, a "block" design composed of a high-density, partially-segmented (for weighted light sharing) scintillation crystal (bismuth germanate) is coupled to four photomultiplier tubes (PMTs). [M E. Casey, et al., "A multicrystal two dimensional BGO detector system for positron emission tomography," IEEE Trans. Nucl. Sci., 33, 460–463 (1986) and S. R. Cherry, et al., "A Comparison of PET Detector Modules Employing Rectangular and Round Photomultiplier Tubes," IEEE Trans. Nucl. Sci., 42, 1064–1068 (1995) and U.S. Pat. No. 5,453,623]. In this design, the scintillation crystal is subdivided into semi-discrete crystals by incomplete cuts which are filled with reflecting material. The PMTs are not position-sensitive and rely on the different depths of the cuts in the scintillation crystal to yield a light distribution on the PMT's which varies linearly with interaction position across the detector. A problem with the block design of current PET systems is that the intrinsic spatial resolution and the spatial sampling of the block is determined by the size of the individual crystals. In order to improve the intrinsic spatial resolution the size of the crystals needs to be reduced. However, with the block design it becomes difficult to decode smaller crystals. Another problem inherent to the block design PET system is that it is fairly bulky, because of the large dimensions of most single channel PMTs.

More recently, high resolution, high sensitivity PET detectors have been constructed by directly coupling the scintillator material 4 to a compact, low-cost, position-sensitive PMT (PS-PMT). By coupling small discrete scintillator elements 4 directly onto the active area of the PS-PMT, one maximizes light transmission from the scintillator 4 to the PS-PMT. [J. J. Vaquero, et al., "Performance Characteristics of a Compact Position-Sensitive LSO Detector Module," IEEE Trans. Nucl. Sci.,17, 967–978 (1998) and R. Pani, et al., "Multi-PSPMT scintillation camera," IEEE Trans. Nucl. Sci., 46, 702708(1998) and U.S. Pat. No. 5,864,141]. However, these PS-PMT's have a significant inactive area at the edges. Using the direct coupling method and tiling many detectors together to form planar arrays, therefore, produces large gaps between the detector modules 20 because the effective or active area 10 of the PMT 8 does not span the full physical dimensions of the face of the tube (FIG. 1a). This reduces system sensitivity and sampling and causes problems in the reconstruction of the data. Therefore, it is desirable to develop some sort of tapered light guide 12 to eliminate these gaps and to form large continuous arrays (FIG. 1b). [R. Pani, et al., supra.]

A PET camera based on discrete LSO scintillator elements and a fixed ring geometry has been reported. [W. Moses, et al., "PET camera designs for imaging breast cancer and axillary node involvement," J. Nucl. Med., 36, 69P (1995) and U.S. Pat. No. 6,040,580]. However, the flexibility of the planar detector arrays with variable separation of the present invention offers advantages in the clinical setting over PET systems in a fixed ring geometry.

Conventional PET imaging devices are designed to image cross sections of the entire body. Although functional imaging with PET is a promising technique in conjunction with x-ray mammography for breast cancer patient management, there are several disadvantages to employing a whole body PET scanner for the detection of malignant breast tumors. The first disadvantage is that the whole body PET system is limited by the spatial resolution and sensitivity. [N. Avril, et al., supra]. Whole body PET systems typically yield reconstructed images with a resolution of 8–15 mm, depending on the injected dose, imaging time, and intrinsic resolution of the scanner. The effect of this resolution limit is that radioactivity is underestimated.

The second disadvantage of a conventional whole body PET is the high cost of the examination. Whole body PET is an expensive technology, and is generally only available in the larger medical facilities in the United States.

A third disadvantage of a conventional whole body PET scanner is that the PET scanner provides metabolic images of breast cancer patients with several shortcomings related to the general-purpose nature of these systems, e.g., in whole body scanners the detectors are typically 20–30 cm away from the breast or axilla, which reduces sensitivity. Conventional scanners also have relatively large detector elements (greater than 4 mm), which limits spatial resolution.

BRIEF SUMMARY OF THE INVENTION

The present invention is an apparatus and method for examining a body part. In particular, the present invention is directed to a dedicated PET system for breast imaging or imaging other body parts, such as the head, neck, liver, heart, lungs and other extremities, which overcomes the limitations of prior detectors and improves the overall diagnostic quality of the images.

The positron emission tomography imaging apparatus of the present invention is a dedicated mammary and axillary region PET imaging system and comprises at least two large-area planar scintillation detector plates composed of 25, a 5×5 array, of modular detectors. The detectors include an array of scintillation crystals, a plurality of photomultiplier tubes positioned adjacent the plurality of scintillation crystals, and a lightguide having an end positioned adjacent to the array of scintillation crystals and having an opposing end adjacent to the photomultiplier tubes.

The planar scintillation detector plates 22 operate in coincidence and have about a 15×15 $cm^2$ surface area, giving complete coverage of the breast in a single view. The detector can be mounted on a flexible gantry, allowing the inter-detector separation to be varied from about 10 cm up to about 50 cm, and also allowing the detectors to rotate to collect tomographic information.

A method for examining a body part is also described and comprises providing an internal image of the body part including, a positron emitting radioisotope and a positron recording apparatus between which the body part is to be disposed; and placing at least two detector plates 22, each plate comprised of at least one detector, said detector having a scintillator coupled to one end of a lightguide, the opposing end of said lightguide coupled to a photomultiplier tube, said detector is capable of detecting gamma-rays emitted by the radioisotope infiltrated into the body part in an adjacent relationship with said recording apparatus for providing the internal image.

The system of the present invention allows for adjustable detector separation to accommodate all patients and permits imaging of the axillary region. The adjustable detector plate separation also allows closeness to the area being imaged, thereby increasing the system sensitivity. The detector plates 22 or arrays are large enough to scan an entire breast in one imaging setup. The flexible scanner geometry allows planar, limited angle, filtered back projection or iterative image reconstruction techniques to be implemented.

The present invention has a number of important advantages over conventional PET scanners. The present invention brings the detectors in close to the breast or axilla, resulting in a large increase in the system sensitivity (the fraction of emitted gamma ray pairs that are detected) which is due to the increase in solid angle. This increase in sensitivity allows for an improved image signal-to-noise and/or image resolution. The increase in sensitivity also results in a reduced imaging time (increasing patient throughput) and/or allows for a smaller injected dose of FDG. Furthermore, the present invention allows for the gamma ray pairs to only pass through the breast to be detected, and does not require them to pass through the entire cross-section of the chest. Therefore, tissue attenuation is reduced and the correction for gamma-ray attenuation can be based on simple geometric calculations. Lastly, because relatively few detector modules 20 are needed to construct the scanner of the present invention (about 50 in the proposed system versus 250–300 in a whole-body PET scanner), the overall cost of the technology is dramatically reduced. This, in conjunction with the widespread availability of FDG from the growing network of PET radio-pharmaceutical distribution centers, results in PET becoming a viable diagnostic tool for breast cancer patient management.

This system offers several advantages when compared with existing dedicated PET systems for breast imaging and conventional whole-body PET scanners. Firstly, LSO scintillators provide important advantages over dedicated systems that use BGO crystals. Lutetium oxyorthosilicate (LSO) scintillators have a decay time of 40 ns which provides count-rate performance advantages. Thus, LSO has similar stopping power to BGO, but produces five times as much scintillation light and has a seven-fold shorter decay time, which enables the detector of the present invention to operate successfully in the high singles count rate environment expected in breast imaging, due to nearby activity from the heart and liver. The increased light output allows good timing and energy resolution improving image quality by reducing the influence of randoms and scatter.

Secondly, the use of an optical fiber taper allows detector modules 20 to be tiled together in planar arrays (with no gaps) which produce detector plates 22 of any desired size. For example, the 15×15 cm² detector plates 22 of the present invention provide a large field of view which provide for better coverage and a shorter imaging time. Furthermore, these plates 22 are sensitive and maintain their resolution right to the very edges, allowing the closest possible imaging of the chest wall and imaging of the entire body part or breast. [C. J. Thompson, et al., "Positron emission mammography (PEM): A promising technique for detecting breast cancer," IEEE Trans. Nucl. Sci., 42, 1012–1017 (1995); C. J. Thompson, et al., "Feasibility study for positron emission mammography," Med. Phys., 21, 529–537 (1994); J. L. Robar, et al., "Construction and calibration of detectors for high resolution metabolic breast imaging," Nucl. Instrum. Methods Phys. Res. A, 392, 402–406 (1997); I. Weinberg, et al., "Preliminary results for positron emission mammography: Real-time functional breast imaging in a conventional mammography gantry," Eur. J. Nucl. Med., 23, 804–806 (1996); R. Freifelder, et al., "Dedicated PET scanners for breast imaging," Phys. Med. Biol., 42, 2463–2480 (1997); and G. Hutchins, et al., "Evaluation of prototype geometries for breast imaging with PET radiopharmaceutical," J. Nucl. Med., 36, 69P (1995)].

The present invention is also surprisingly inexpensive, as the tapered optical fiber bundles used in this work are a fraction of the cost of the very high resolution tapers used in conventional CCD based imaging systems. Lastly, the large-area plate geometry with variable separation allows unprecedented flexibility for clinical applications. The detector separation can be adjusted to suit the patient geometry and planar, limited angle or full tomographic datasets of the breast can be acquired. Planar images of the axilla may also be acquired with our proposed system. Bringing the detectors in close to the object of interest will improve sensitivity relative to whole-body PET scanners, and the resolution and timing performance of our detector modules 20 has been demonstrated to be superior to that measured in whole-body PET detectors. The goal of the maxPET system is to aid in breast cancer patient management by assisting in imaging patients with dense, fibro-glandular breasts, detecting axillary lymph node metastases without surgery and monitoring chemotherapy effectiveness.

These and other features, aspects, and advantages of the present invention will become better understood with regard to the following detailed description, appended claims, and accompanying drawings.

BRIEF DESCRIPTION OF THE DRAWINGS

FIG. 6 shows an assembled detector module, having a 9×9 array of about 3×3×20 mm³ LSO crystals coupled through a tapered optical fiber bundle to a Hamamatsu R5900-C8 PS-PMT;

FIG. 7 shows the flood histogram which was obtained by uniformly irradiating the detector module with a $^{22}$Na point source 14 whereby all 81 crystals from the LSO scintillator array are clearly visible;

FIG. 11 shows two planar detector plates having 5×5 arrays of the modular detectors used in the PET imaging system of the present invention;

FIG. 12 shows the maxPET detector assembly comprising two opposing 15 cm×15 cm LSO detector plates mounted about 15 cm apart in an aluminum frame;

16a is reconstructed with a full acceptance angle and FIG. 16b is reconstructed with a half angle of acceptance; FIG. 17a is taken from FIG. 16a and shows a resolution of about 4 mm, FIG. 17b is taken from FIG. 16b and shows a resolution of about 5.5 mm.

DETAILED DESCRIPTION OF THE INVENTION

Figure 1A:
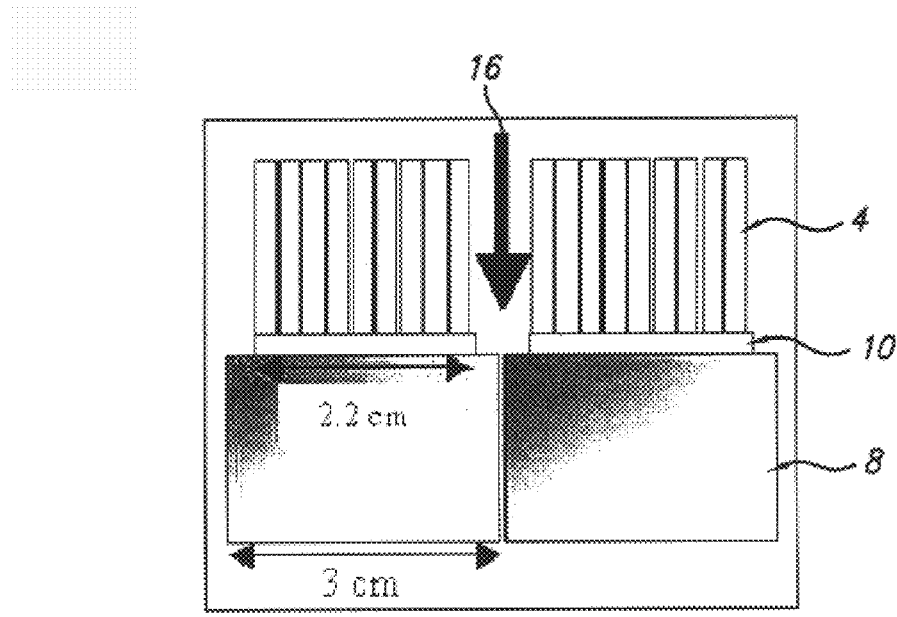
FIG. 1a shows the direct coupling of scintillator arrays into the photomultiplier tube 8 (PMT)

The maxPET system of the present invention comprises at least two 15×15 cm$^2$ planar scintillation detector plates 22 operating in coincidence, with each plate composed of a 5×5 array (25) modular detectors (FIGS. 11 and 12). Each modular detector is composed of three individual components: a photomultiplier tube, a lightguide 12, such as an optical fiber bundle, and a scintillator array. The scintillator array is comprised of a 9×9 array of about 3×3×20 mm$^3$ lutetium oxyorthosilicate (LSO) scintillator crystals 4 or detector elements, which are coupled to the lightguide 12, such as the optical fiber bundle, which in turn is coupled to the position-sensitive photomultiplier tube 8 (PS-PMT), such as the Hamamatsu R5900-C8. The modular detectors are thus read out by a 5×5 array of PS-PMT. A mutliplexing readout scheme is also utilized to reduce the number of readout channels from 200 (4X and 4Y readouts per PS-PMT) to 8 channels per plate.

Although LSO crystals 4 are preferred, other light-output equivalent crystals may be used, such as gadolinium oxyorthosilicate (GSO), bismuth germanate (BGO), LGSO (a mixture of BGO and LSO), yttrium aluminum pyrovskite (YAP), and sodium iodide (NaI(TI)). In another embodiment of the invention, the detectors are tiled together, without gaps, to construct large area detector arrays to form a dedicated PET cancer imaging system, preferably a breast cancer imaging system. All detector elements are clearly visualized upon flood irradiation of the module.

Thus, the dedicated PET system of the present invention takes advantage of the high specificity of FDG PET imaging and, at the same time, improves the sensitivity for breast cancer detection by improving the image resolution to about 3 mm or better. The use of smaller detector elements also improves the resolution. It is also possible to rotate the planar detectors around the breast to obtain fully sampled datasets to allow tomographic reconstruction.

By using a LSO scintillator, a novel lightguide 12 coupling method, and an efficient way to construct the scintillator array, the PET modular detector of the present invention has a measured intrinsic spatial resolution (full-width at half maximum) of about 1.8–2.6 mm, typically about 2.26 mm, an average energy resolution of about 17–24%, typically about 19.5% at 511 keV and a coincidence timing resolution of about 2.4 ns. The detector efficiency was about 53% for 511 keV gamma rays, using an energy threshold set slightly above the electronic noise. These measurements equal or exceed those obtained from conventional whole-body PET detector designs. Over 95% of the 4050 crystals in the system of the present invention can be identified in flood histograms of the detector plates 22. The coincidence timing resolution for the entire system is 8.1 ns.

I. Detector Design

A. Photomultiplier Tube

Figure 1B:
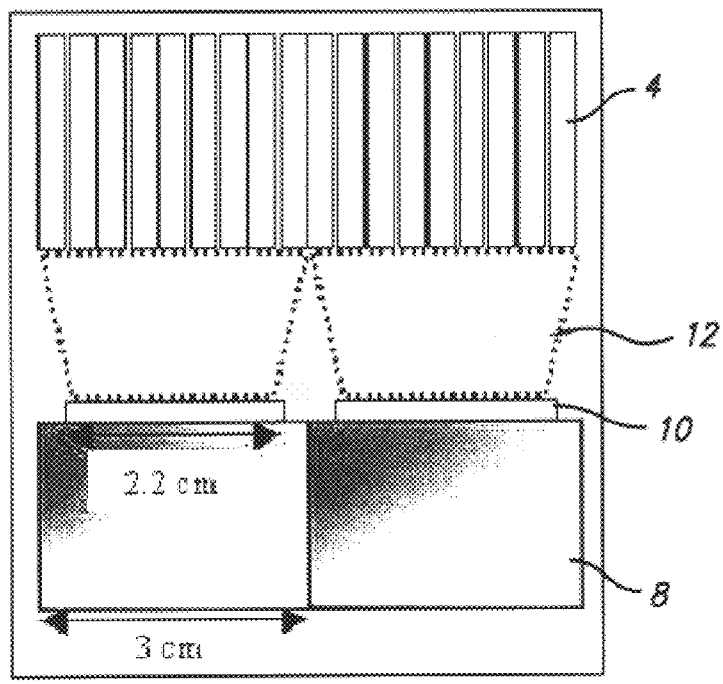
FIG. 1b shows the use of a tapered light guide to couple the light from the scintillator array into the PMT 8.
Figure 2:
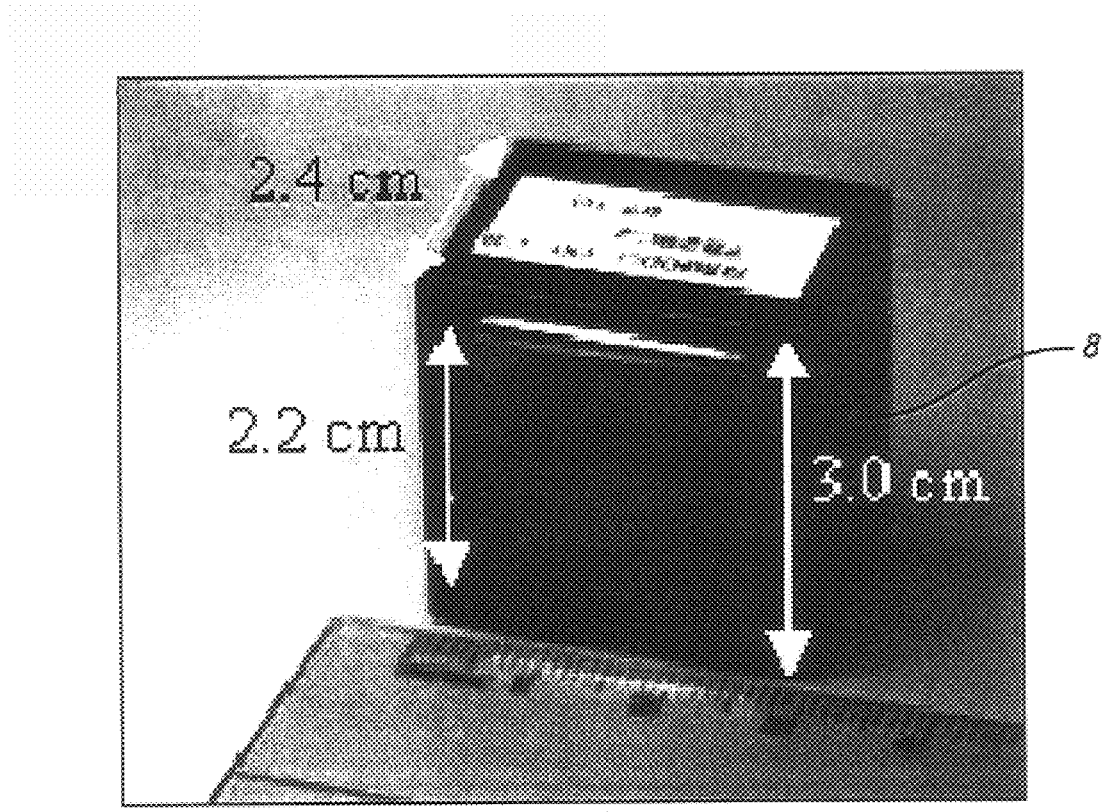
FIG. 2 shows a position-sensitive PMT 8 (PS-PMT) with a physical surface area measuring about 3×3 cm² and an active area of about 2.2×2.2 cm².

The PS-PMT 8 chosen for the detector module 20 was the Hamamatsu R5900-C8 (manufactured by Hamamatsu Photonics K.K., Japan) which had a 4+4 cross plate anode arrangement and 11 dynode stages with an approximate gain of 6×10$^6$ at −800V, shown in FIG. 2. The photocathode's maximum response was at about 420 nm, which corresponded well to the light emission spectrum of LSO. The physical surface area of the PS-PMT 8 was about 3×3 cm$^2$, and the active photocathode area of the tube was about 2.2×2.2 cm$^2$. Because there was a discrepancy between the active area of the tube and the total surface area size, a one-to one coupling of the scintillation crystals 4 to the active area resulted in a large dead space 16, equal to about 1.6 cm between two adjacent PS-PMTs 8, seen in FIG. 1a. In order to allow close packing of the detector modules 20 without any gaps (FIG. 1b), a scintillator crystal array 4 that matched the outer surface area of the PS-PMT 8 was used. The coupling of the array to the active area of the PS-PMT 8 is described in section C.

B. Scintillator Array

Conventionally, scintillator arrays have been formed from polished crystals that are either hand-wrapped in reflective PTFE tape and bundled together, or alternatively, glued together using a white pigment, such as BaSO$_4$ or TiO$_2$ mixed with an epoxy or RTV. The disadvantage of the approach of wrapping in reflective PTFE tape is that it is extremely labor intensive and difficult to control. The disadvantage of the latter approach, bonding the reflective pigment onto the surfaces of the crystal 4, is that light output is reduced substantially. Also, the mechanical polishing of large numbers of small crystals is also an expensive process.

The arrays of the present invention were formed using a different approach, designed to reduce the cost and labor involved, while maintaining high light output. The dimensions of the LSO crystals 4 were about 3×3×20 mm$^3$. Slabs of raw LSO were initially cut to about 3×3×20 mm$^3$ in size and then chemically polished, rather than mechanically polished using abrasives. The chemical polishing technique required bathing the crystals in phosphoric acid, the concentration of which was 85% by volume, for about 16 minutes at 190° C. [R. Slates, et al., "Chemical Polishing of LSO Crystals to Increase Light Output," IEEE Trans. Nucl. Sci., 47, 1018–1023 (2000); J. S. Huber, et al., "Geometry and Surface Treatment Dependence of the Light Collection from LSO Crystals," Nucl. Inst. Meth., 437, 374–380 (1999); and K. Kurashige, et al., "Surface Polishing of GSO Scintillator Using Chemical Process," IEEE Trans. Nucl. Sci., 45, 522–524 (1998)]. The chemical polishing resulted in equivalent or increased light output compared with mechanical polishing.

Figure 3:
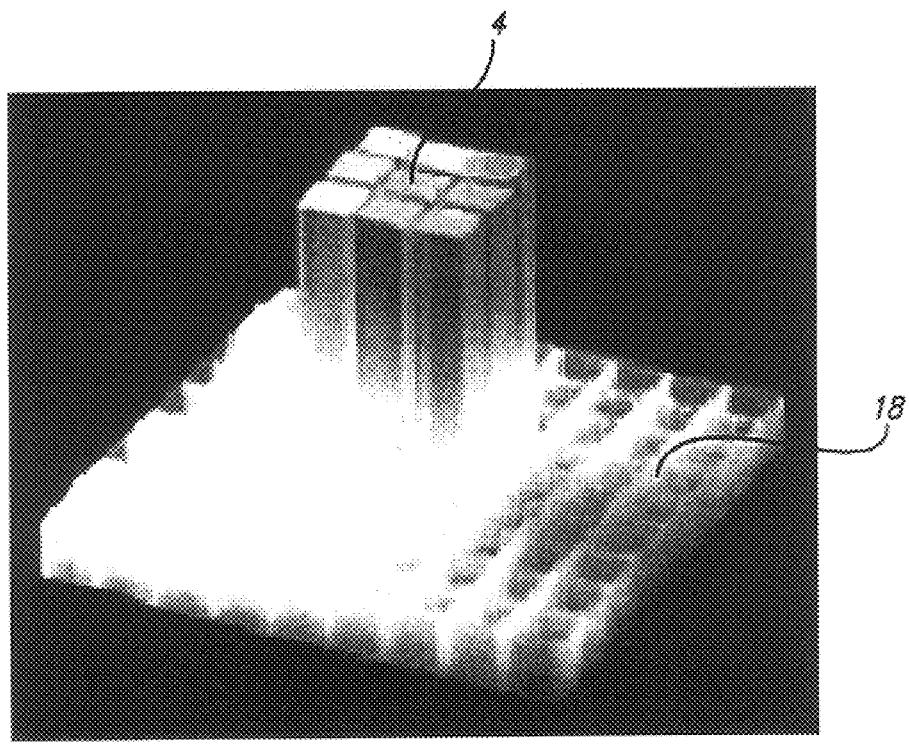
FIG. 3 shows a plastic grid (manufactured by Stratasys Inc., Eden Prairie, U.S.A.) with a 9×9 matrix of square holes that measure about 3×3×5 mm³ and a wall thickness of about 0.3 mm; 9 of the 81 lutetium oxyorthosilicate (LSO) crystals are shown placed in the holes of the grid.

The scintillator array of the present invention included a 9×9 matrix of individually cut LSO crystals 4. To form the array, a plastic grid 18 was used in order to hold the chemically polished crystals in place. The grid 18, shown in FIG. 3, consisted of a matrix of 9×9 square holes of a size about 3×3 mm$^2$ with a wall thickness of about 0.3 mm (the gap between the crystals). The height of the grid 18 was about 5 mm. The grid 18 was fabricated using a 3-D stereolithography system (manufactured by Stratasys Inc., Eden Prairie, U.S.A.) which used a very fine extrusion process to build multi-layered objects. Each crystal 4 was encapsulated in white reflective material on the five sides not coupled to the PS-PMT 8, to enhance the light output from the side or end from which the scintillation light crystal 4 was coupled into the PS-PMT. The reflective material was BaSO$_4$ powder and methanol in a 1:1 mixture by weight. The thickness of the reflective material was 300 μm which resulted in overall array dimensions of about 3×3 cm$^2$ that matched the physical dimension of the PS-PMT, which enabled detector modules 20 to be tiled together without gaps. Thus, once the crystals 4 were placed in the grid 18, the 300 μm gap between the crystals 4 was filled with a slurry of reflective material, $BaSO_4$ powder and methanol in a 1:1 mixture by weight. $BaSO_4$ has an extremely high reflectivity in about the 400–500 nm wavelength range. [W. Budde, "Standards of Reflectance," J. Opt. Soc. Am., 50, 217–220 (1960)]. The crystal array 4 was left overnight, during which time the methanol evaporated and left a uniform coating of $BaSO_4$ on the crystals. The outer four sides of the crystal array 4 were then wrapped in PTFE tape. The top of the array was also covered with PTFE tape or powder to provide high reflectance.

C. Crystal/PMT Coupling Arrangements

Conventional crystal/PMT arrangements involve the placement of the outer edge of a PMT adjacent to and aligned with the outer edge of an array of scintillation crystals. By constructing a scintillator array that matched the physical area of the PMT in the present invention, the dimensions of the crystal array 4 now exceeded the active area of the PMT, which read out the crystal array 4. Thus, it was necessary to minify the light distribution from the crystal array so that it could be read by the PMT. This was accomplished by refocusing or tapering of the light from the about $3 \times 3$ $cm^2$ surface area down to about a $2 \times 2$ $cm^2$ surface area using a lightguide 12, while still maintaining the spatial coherence of the light emitted by the individual crystals.

High efficiency of light transmission through the lightguide 12 is of vital importance to preserve energy and timing resolution in the detector. These directly impact the ability of the PET system to reject scattered events and to reduce the occurrence of random coincidence events. A further constraint to overcome was that the surface area of the lightguide 12 should be no larger than $3 \times 3$ $cm^2$, so that multiple individual detector modules 20 can be tiled together into a larger detector array. In order to determine the optimal configuration for coupling the scintillation crystals to the PMT face, five different arrangements were tested.

EXAMPLE 1

Figure 4A:
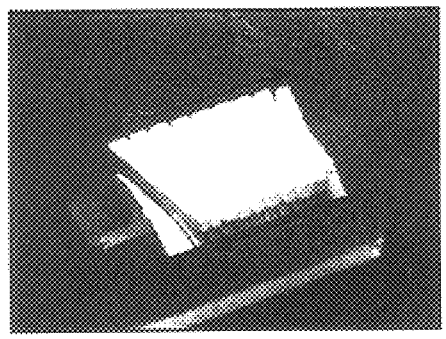
FIGS. 4a to 4f are light guides, used to couple the about 3×3 cm² scintillation array down to the about 2×2 cm² active area of the PMT 8, showing: tapered LSO crystals 4 (FIG. 4a); individual tapered light guides made from glass (FIG. 4b); a piano-concave lens (PCV) cut into about a 3×3 cm square (FIG. 4c); individual optical fibers (FIG. 4d); a tapered optical fiber bundle having one end about 5.3 cm in diameter (FIG. 4e); and a tapered optical fiber bundle having one end of about a 3×3 cm square, made by cutting down the 5.3 cm end of FIG. 4e (FIG. 4f)

Tapered LSO crystals were directly coupled to the PMT face. Nine rectangular crystals of a size about $3 \times 3 \times 20$ $mm^3$ were taken and cut with the aid of a diamond saw into a tapered form to match the active area of the PMT (FIG. 4a). Each individual crystal had been chemically polished and wrapped in polytetrafluoroethylene (PTFE) tape (such as TEFLON, manufactured by Dupont, U.S.A). The unwrapped side or face was coupled to the PMT with the aid of optical grease (index of refraction of about 1.433). This arrangement served as a good reference with which to measure the degradation introduced by the coupling arrangements described below.

Lightguide 12 Arrangements

EXAMPLE 2

Figure 4B:
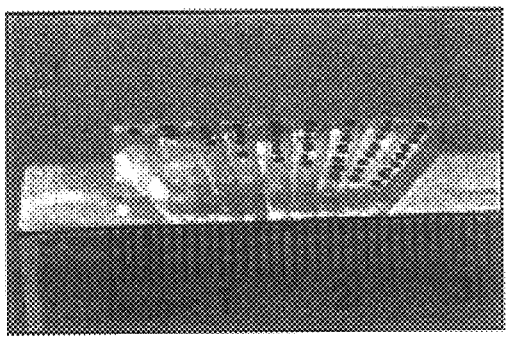

A lightguide 12 constructed from B-270 glass (Precision Glass and Optics, Santa Ana, Calif., U.S.A.) cut into individually tapered lightguides 12 was used (FIG. 4b). This particular glass is available in large sizes for machining and has good transmission in the blue part of the spectrum where LSO emits most of its light. The dimensions of the lightguide 12 were cut so that one side would match the scintillation crystal array (about 3 cm) and the other side would match the active face of the PMT (about 2 cm). Both interfaces, between the lightguide 12 and PMT 8 and between the lightguide 12 and the crystal array 4, were coupled with optical grease.

EXAMPLE 3

Figure 4C:
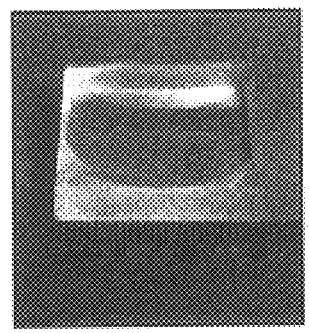

A conventional optical lens (Edmund Scientific, Barrington, N.J.) was utilized. A central square section of size about 30 $cm^2$ was cut out of a plano-concave (PCV) lens of diameter about 50.0 mm and having an effective focal length of about −100.0 mm (FIG. 4c). The curved surface of the lens was placed directly on the PMT. The crystal array was coupled to the planar side of the lens using optical grease.

EXAMPLE 4

Figure 4D:
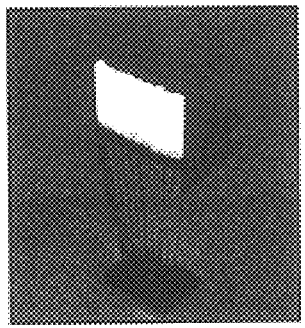

A set of nine, double-clad optical fibers (Kuraray Corp., Japan) about 2 mm diameter and about 5.3 cm long were utilized (FIG. 4d). The indices of refraction for this fiber were about 1.59 (core), about 1.49 (inner cladding) and about 1.42 (outer cladding), giving a numerical aperture of about 0.72. This configuration was similar to that used in a detector previously developed for small animal imaging. [S. R. Cherry, et al., "Optical fiber readout of scintillator arrays using a multi-channel PMT: A high resolution PET detector for animal imaging," IEEE Trans. Nucl. Sci., 43, 1932–1937 (1996)]. All interfaces, as in Example 2, were coupled with the aid of optical grease.

EXAMPLE 5

Figure 4E:
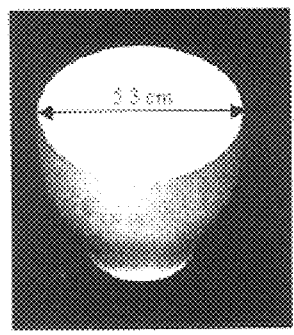
Figure 4F:
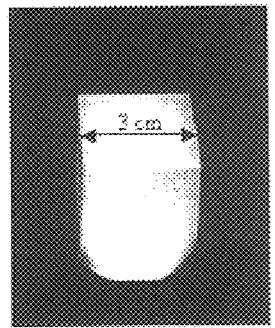

A tapered fiber bundle (TaperVision Inc., Pomfret, Conn.), as shown in FIG. 4e, was used. The optical fiber bundle was a coherent bundle composed of many thousands of micron diameter glass fibers fused together. To allow detector modules 20 to be tiled together, the larger end of the fiber taper, FIG. 4e, was cut into about a $3 \times 3$ cm square to match the physical dimensions of the PMT and the LSO array, as shown in FIG. 4f. The taper was made from thousands of 10 micron diameter glass fibers that were vacuum fused and then drawn out to form the tapered end while maintaining spatial coherence of the light. [E. Peli, et al., "Fiber-optic reading magnifiers for the visually impaired," J. Opt. Soc. Amer. A, 12, 2274–2285 (1995)]. The light transmission at about 420 nm, as measured with a spectrophotometer, was about 30% with a numerical aperture of about 0.98. The larger diameter of the uncut taper, FIG. 4e, was about 5.3 cm and the smaller diameter measured about 2.9 cm, therefore the effective minification factor was about 1.8.

RESULTS OF COUPLING ARRANGEMENTS EXAMPLES

Each of the five coupling methods described above was evaluated. Energy resolution, light collection efficiency, and the identification of the individual elements in the scintillator array were measured.

Figure 5A:
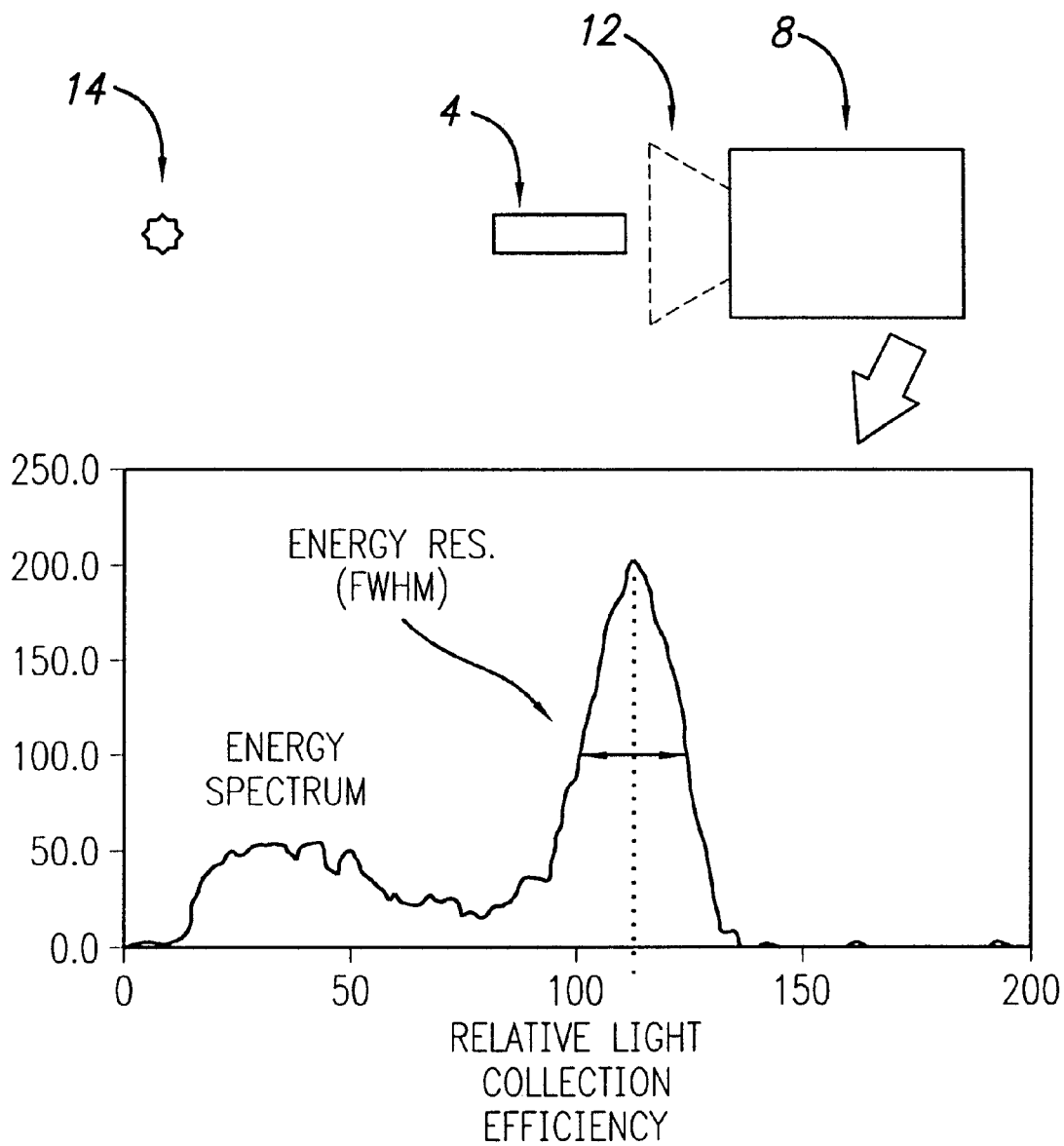
FIG. 5a is a schematic representation illustrating the measurement of the energy resolution and the light collection efficiency.

To measure the energy resolution and light collection efficiency, a single about $3 \times 3 \times 20$ $mm^3$ LSO crystal was used in conjunction with the different coupling arrangements. A $^{22}Na$ point source 14 was placed about 10 cm from the proximal face of the LSO crystal and an energy spectrum was acquired. From the energy spectrum, the full-width at half maximum (FWHM) of the 511 keV photopeak was measured to provide the energy resolution. The relative position of the photopeak, with respect to that obtained with the LSO directly coupled to the PMT, was used to measure the light collection efficiency. A schematic diagram of this measurement is shown in FIG. 5a.

Figure 5B:
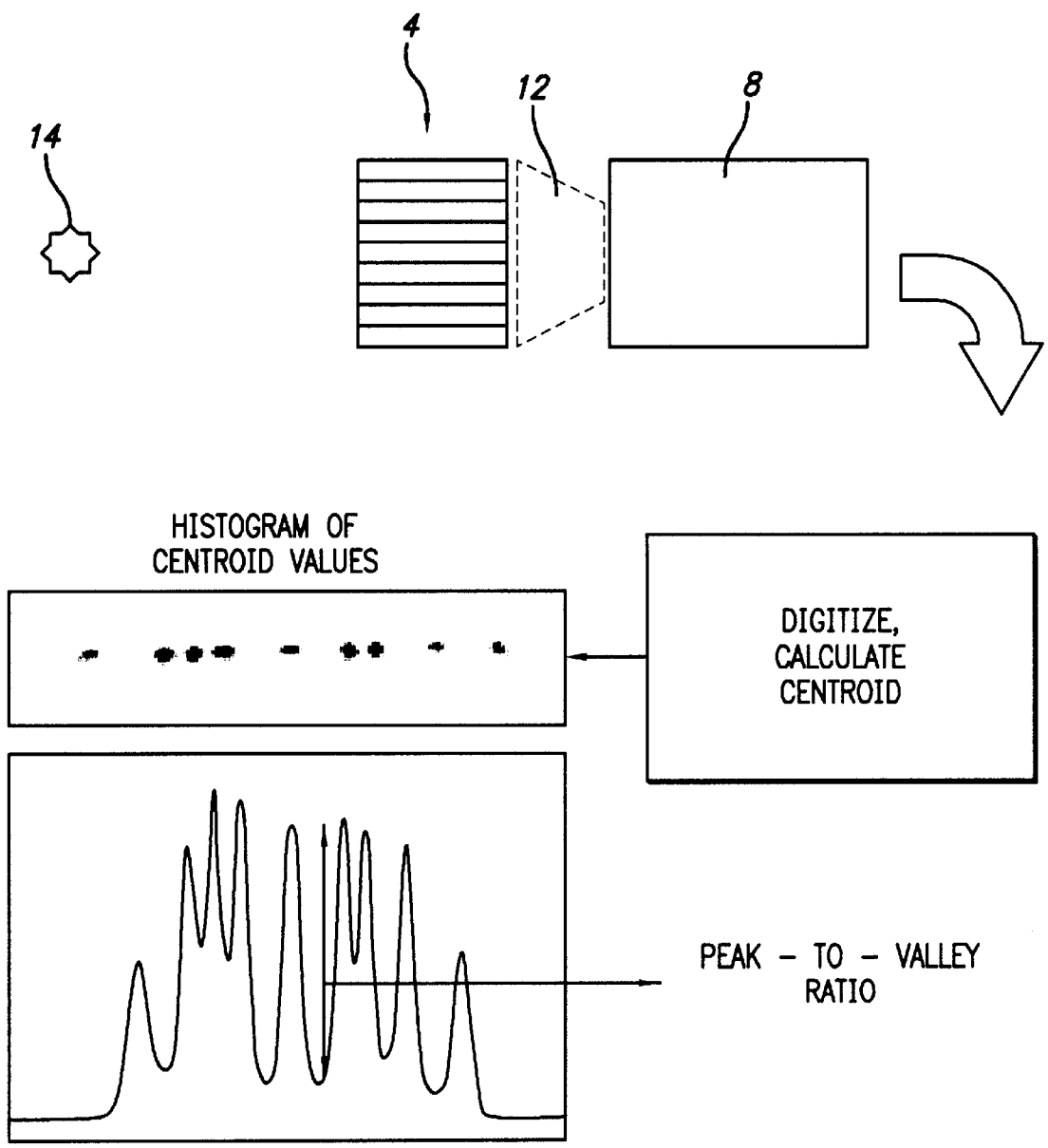
FIG. 5b is a schematic representation illustrating the measurement of the flood histogram and the peak-to-valley ratio.

To assess the identification of individual elements in the scintillator array, a one dimensional array of nine about 3×3×20 mm³ in size LSO crystals was coupled to the PS-PMT using the coupling arrangements described above and compared with direct coupling of tapered LSO crystals to the PS-PMT (FIG. 5b). The array was flood irradiated with a $^{22}$Na point source 14. For each detected event, the four outputs of the PS-PMT corresponding to the direction of the array on the PS-PMT face were digitized and the centroid position calculated. The histogram of the centroid positions for a large number of events was examined to see if the individual crystals can be separated. A profile through the histogram provided a more quantitative assessment of crystal identification by measuring the peak to valley ratio. Only the central three crystals were used to measure the average peak-to-valley ratio, as the nine crystals could not all be identified with every coupling scheme.

To minimize variability between measurements, the same LSO crystals, PMT and electronics were used throughout all of the experiments. The high voltage bias to the PMT, constant-fraction discriminator setting, and timing gate width were all kept constant. The measurements of the various figures-of-merit (energy resolution, light collection and flood histogram peak-to-valley ratio) for the different experimental setups are presented in Table I.

TABLE I

Summary results from the various lightguide configuration experiments

| Coupler | Energy Resolution (FWHM %) | Light Collection Efficiency (%) | Average Peak-to-Valley Ratio | Number of Crystals Clearly Resolved |
|---|---|---|---|---|
| Direct LSO* | 13.0 | 100.0 | 10.0 | 9 |
| Lightguide* | 19.9 | 40.6 | 2.5 | 8 |
| PCV Lens | 27.2 | 28.0 | 2.5 | 7 |
| Fiber* | 35.0 | 12.6 | 6.0 | 6 |
| Fiber taper | 19.5 | 27.0 | 7.5 | 9 |

*Energy resolution and light collection efficiency were measured with single lightguide elements.

Compared to direct coupling, the best combination of energy resolution and crystal identification was obtained with the tapered fiber bundle, which was also able to clearly resolve all the individual crystals in the flood histogram. The measured energy resolution was about 19.5% with a light collection efficiency of about 27% compared with direct coupling. The tapered fiber bundle was a relatively inexpensive solution and was very easy to handle. Individual light guides had better light collection efficiency, but the energy resolution was not significantly better than the tapered fiber bundle and the crystals were poorly resolved, as indicated by the inferior peak-to-valley ratio.

E. Construction of the Detector Module

Based on the results of the coupling examples, two complete detector modules 20 were constructed. The scintillator array was formed as described further, in section II.A, and coupled through the optical fiber taper, shown in FIG. 4e, to the R5900-C8 PS-PMT. A completed detector module 20 is shown in FIG. 6. The fully assembled detector module 20, including the PMT socket containing the dynode resistor chain bias network, was about 3 cm long, about 3 cm wide, and about 9.75 cm long.

II. Detector Module Characterization

A. Flood Source Histogram

One of the constructed detector modules 20 was uniformly irradiated with a $^{68}$Ge point source. The position signals from the PS-PMT (4 X and 4 Y outputs) were multiplexed to give 2 X and 2 Y outputs with the use of a simple resistive chain readout configuration. The four position signals were integrated for about 0.2 µsec and fed into an analog-to-digital conversion (ADC) board (Model PCI-416L manufactured by Datel Inc., Mansfield, U.S.A.) located inside the data acquisition computer (Model Optiplex GX1P manufactured by Dell Computers, Inc., Round Rock, U.S.A.). The X and Y coordinates were calculated for each detected event according to Anger logic and histogrammed to produce a 2-D position map. [$^{30}$H. Anger, "Scintillation cameras," Rev. Sci. Instr., 29, 27–33 (1958)]. The lower energy threshold was set to about 100 keV with the aid of the constant fraction discriminator and no upper energy threshold was applied.

Results

An image of the flood histogram from one detector module 20 is shown in FIG. 7. All 81 crystals from the 9×9 LSO array were clearly visible. An average peak-to-valley ratio of 3.5 was obtained over the central row of 9 crystals. Not all crystals were uniformly spaced in the flood histogram. This may be a result of the non-uniform tapering of the optical fiber taper or the non-uniform packing of the reflectance powder between the crystals. Also, there were variations in gain, light sharing, and position linearity across the PMT. However, each crystal was clearly identified and a position look-up table (LUT) can be easily created from the flood image.

B. Energy Spectra

Boundaries were drawn on the 2-D position map to define a look-up table (LUT) which relates position in the 2-D histogram to the appropriate element in the LSO array. The raw list mode data was then resorted and a histogram of total pulse amplitudes (sum of the four position outputs) was generated for each crystal in the array. These energy spectra were analyzed to determine the FWHM and the location of the 511 keV photopeak of each crystal, these two parameters measured the energy resolution and light collection efficiency, respectively.

Results

Figure 8A:
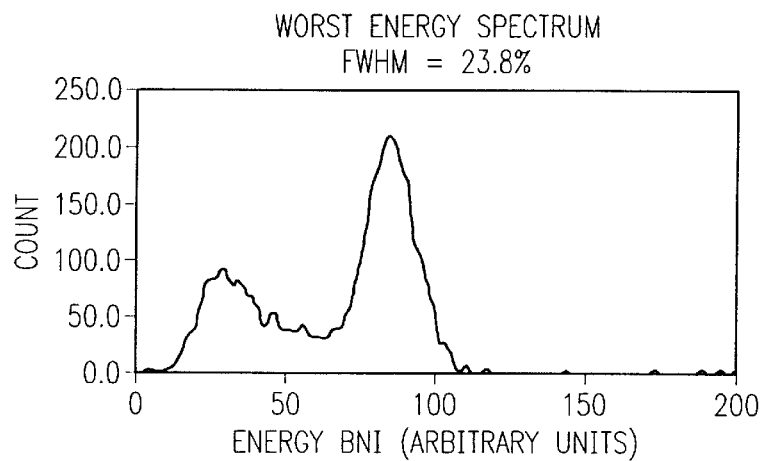
FIGS. 8a to 8c are energy spectra graphs from the 81 crystals from the 9×9 LSO array, the full-width at half maximum (FWHM) of the 511 keV photopeak was measured to provide the energy resolution, showing: the highest energy spectrum of about 23.8% (FIG. 8a); the average energy spectrum of about 19.5% (FIG. 8b); and the lowest (best) energy spectrum of about 17.1% (FIG. 8c)
Figure 8B:
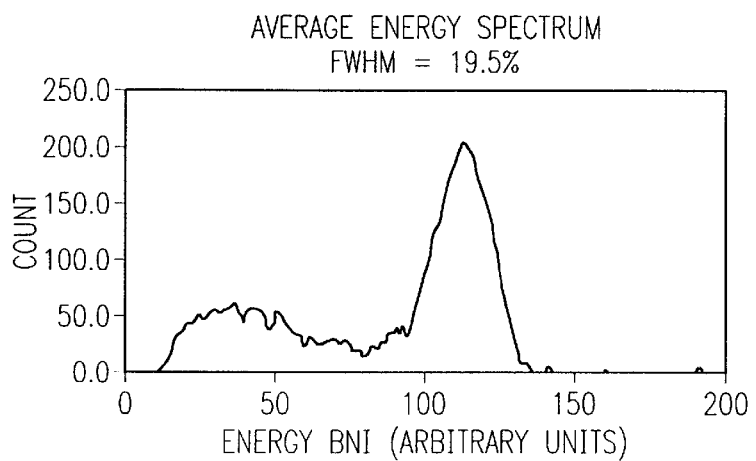
Figure 8C:
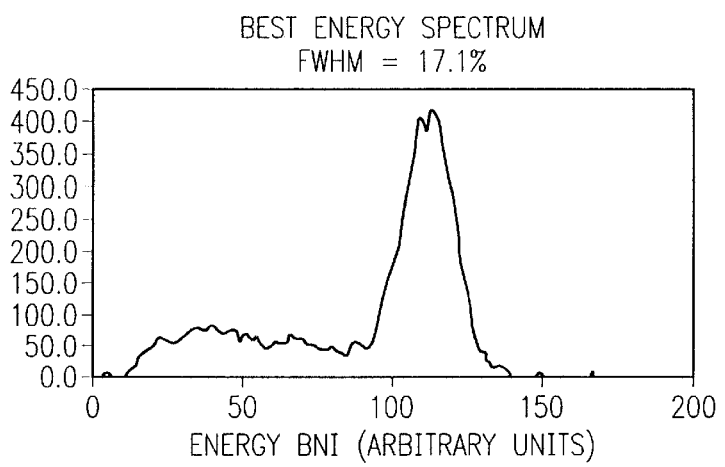

Energy spectra showing the worst, best and an average measurement from the 81 crystal elements are presented in FIG. 8. The average energy resolution for the entire detector module 20 was about 19.5%. This compared very favorably with the 20% energy resolution measured in the detectors used in ECAT EXACT HR+, a clinical whole-body scanner. [S. R. Cherry, et al., supra].

C. Timing Resolution

Two detectors were mounted in an aluminum frame and aligned facing each other in coincidence, a distance of about 15 cm apart (FIG. 12). A $^{22}$Na point source 14 was placed in the center of the two detectors. For each detected coincidence event, the sum of the four position signals for each detector was sent to constant fraction discriminators which generated timing pulses. These two timing pulses, one for each module, were in turn fed into a calibrated time-to-amplitude converter (TAC) module. The output from the TAC was then digitized to produce the timing spectrum.

Results

Figure 9:
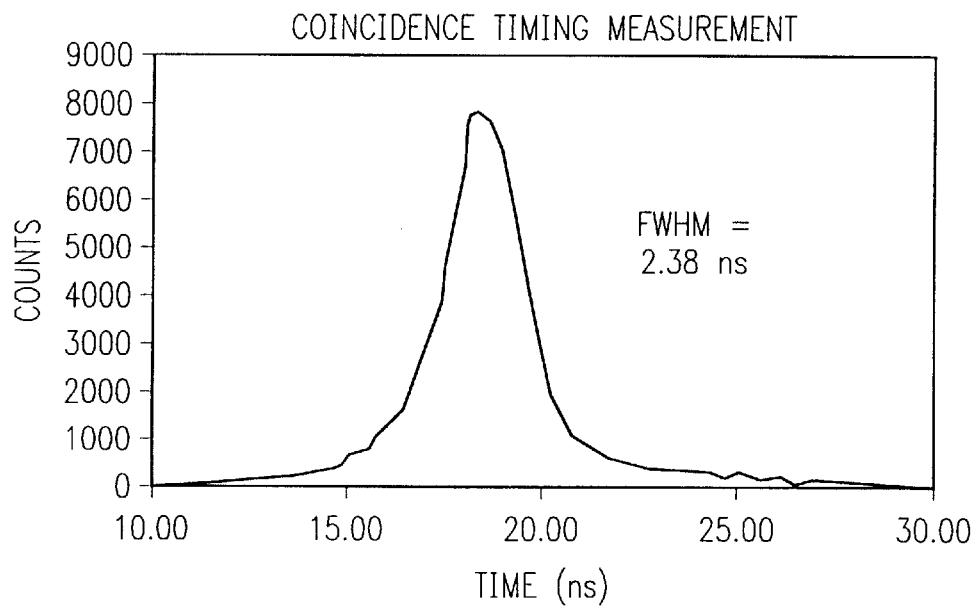
FIG. 9 shows a coincidence timing distribution from two complete modules using a calibrated time-to-amplitude converter (TAC), the timing resolution, measured as the FWHM of the distribution is about 2.38 ns.

The timing spectrum is shown in FIG. 9. The FWHM of the time response was about 2.4 ns. Typical BGO block detectors, those used in conventional whole body PET scanners, have a timing resolution of about 4–6 ns, e.g., the EXACT HR+ has a timing resolution of 5.5 ns. [S. R. Cherry, et al., supra]. Therefore, this new detector design allows better rejection of random coincidence events, as the system timing window can be reduced.

D. Coincidence Point Spread Function

Flood source histograms of both detectors were obtained, as described above in section II.A, from which the position LUT's were defined. The detectors were then connected in coincidence, about 15 cm apart, and list-mode data was acquired by stepping an about 1 mm diameter $^{22}$Na point source 14 between the detectors in about 0.254 mm steps. For each opposing crystal pair, the counts were recorded as a function of the point source position. A lower energy window of about 100 keV was applied. The FWHM of the resulting distribution for each crystal pair was determined to provide the intrinsic spatial resolution of the detectors.

Results

Figure 10:
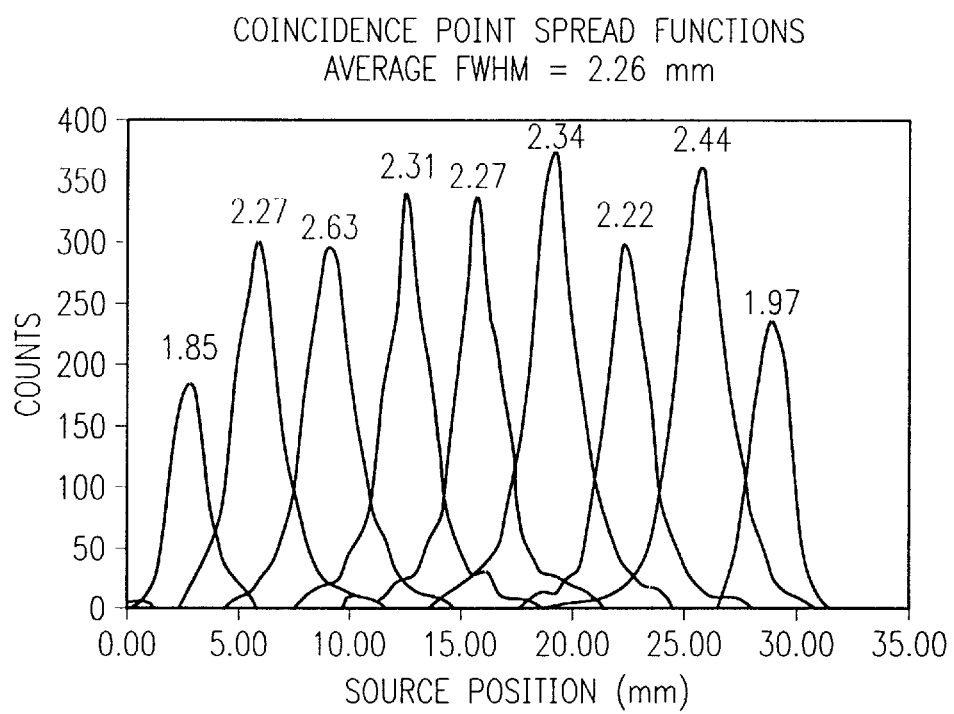
FIG. 10 is a plot of the coincidence point spread function across a row of crystals in the detector module, showing an average spatial resolution of about 2.26 mm, the edge crystals have a better resolution because of the reduced influence of inter-crystal scatter.

The coincidence point spread function for an entire row of crystals is shown in FIG. 10. The average FWHM was measured to be about 2.3 mm, with the worst being about 2.6 mm. The edge crystals tended to have better intrinsic spatial resolution, most likely due to reduced inter-crystal scattering from the adjacent crystals, lowering the probability of mis-positioning events at the edges and corners of the module.

E. Detector Efficiency

A measure of the detector efficiency was performed. A $^{68}$Ge point source with known activity was placed about 9.5 cm away from the face of the detector module 20. The actual photon flux impinging on the detector face was calculated from the solid angle subtended by the detector at the source. The constant fraction discriminator was set to eliminate electronic noise and the number of counts detected by the module was recorded. The number of counts detected was then divided by the number of photons impinging on the detector module 20 to obtain the detector efficiency.

Results

The detector efficiency was calculated to be about 53%. This result coincided well with calculations for the geometry of our module. Based on this measurement, a coincidence efficiency of $(0.53)^2=0.28$, or about 28% is expected, with a wide energy window. The energy window will ultimately depend on the trade-off between efficiency and scatter. This efficiency, when combined with the large solid angle or our proposed system, leads to excellent system sensitivity.

III. System Characterization

Two maxPET detector plates 22 were mounted in an aluminum frame a distance of about 15 cm apart. Alternatively, the two detector plates 22 can be mounted on a gantry allowing variable plate separation, detector plate rotation, and angular motion. The detector plates 22 were connected through NIM pulse shaping electronics to a PC-based data acquisition system running LabView (National Instruments, Austin, Tex.), containing a 16-channel PCI-based ADC board (PCI-416L,Datel Inc., Mansfield, Mass.).

A. Readout Scheme

The design for the maxPET readout electronics involves using commercially available modules and boards. In order to reduce the number of channels to be digitized, the detector plates 22 utilized a modified resistor chain readout scheme based on segmentation of the 5×5 array. Since each PMT produced 8 anode outputs (4X and 4Y), a total of 200 channels (8 anodes×25 tubes) per plate needed to be digitized if each tube was handled individually. To digitize every channel is an impractical and costly approach. Therefore, a multiplexing scheme to reduce the number of channels was again implemented. No more than 4 PMTs were used per readout segment in an attempt to offset multiplexing losses while still significantly reducing the number of readout channels.

Figure 13:
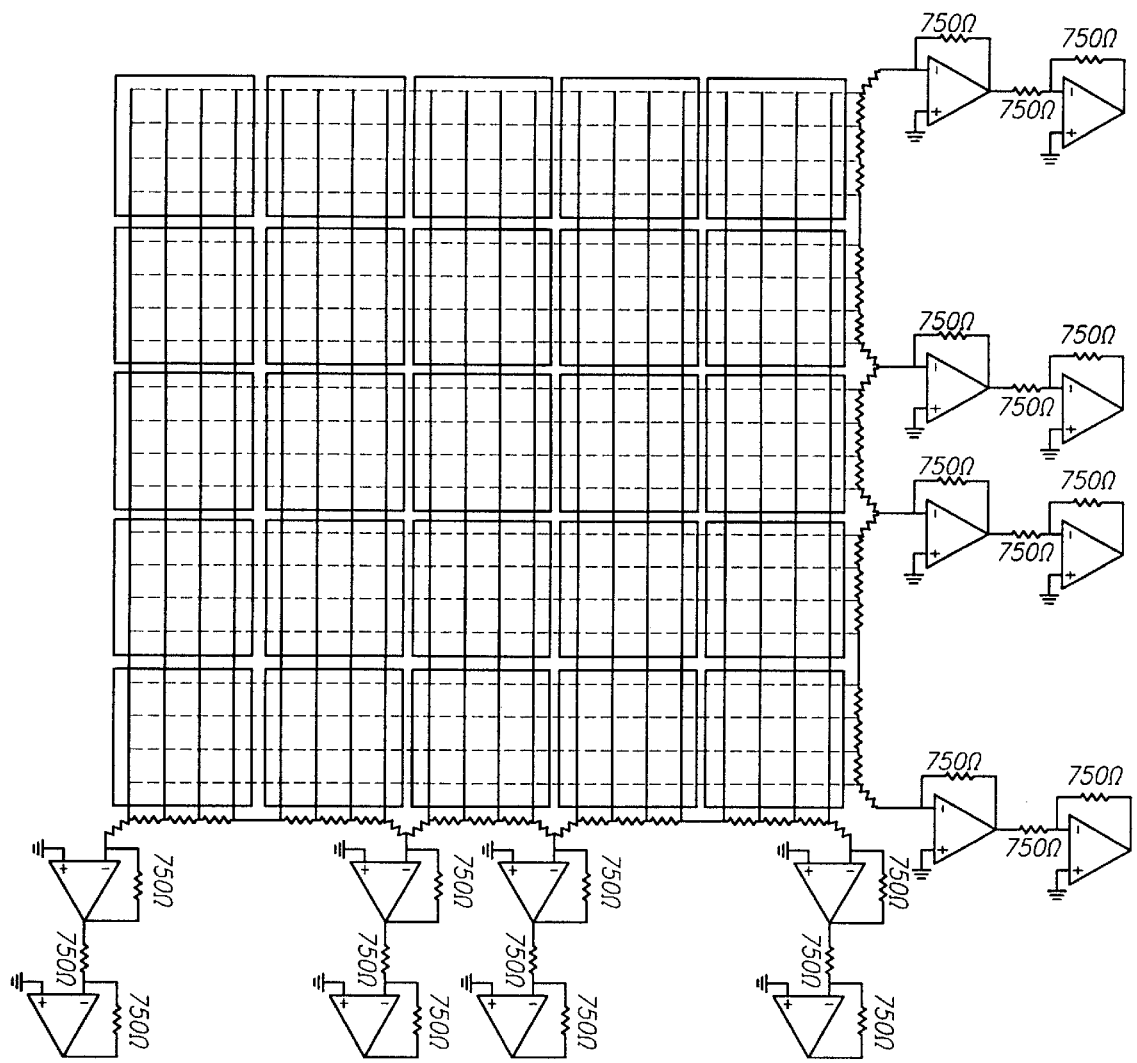
FIG. 13 is the charge division scheme illustrating the multiplexed readout scheme of the detectors.

The multiplexing scheme is seen in FIG. 13. In this approach, the X anodes from all the PMTs along a row were connected together along separate bus lines and then fed into a resistor chain. Similarly, the Y anodes along a column were connected together along separate bus lines and then fed into another resistor chain. There were four summing junctions connected to each resistor chain, producing a total of 8 outputs to be digitized per plate. Each resistor chain utilized 100 ohm resistors in between the anode outputs and 750 ohm resistors in the operational amplifier feedback circuitry. There were two operational amplifier stages. The first stage was a current feedback amplifier and the second stage was a unity gain inverter. The inverter stage produced a negative polarity pulse which is required by the pre-amp input. Rather than using two separate operational amplifiers, a single, surface mount, dual OpAmp (Model AD8015, Analog Devices, Norwood, Mass.) was used.

The resistor chain readout scheme effectively segmented the entire 5×5 array into a total of 9 sectors. This scheme allowed each sector to utilize the full dynamic range of the digitizer thereby allowing better crystal identification. A slightly modified Anger logic algorithm was used to position the event using this readout scheme. Since all 8 channels in the X and Y directions were digitized, the algorithm first determines which sector registered the largest signal output. This is accomplished by summing the two "end" channels per sector and comparing the sum to the other two sectors in that direction. Once the sector which produced the highest signal output for a particular event is determined, conventional Anger logic was only applied to the channels coming from that sector.

B. Flood Histograms

Figures 14A, 14B:
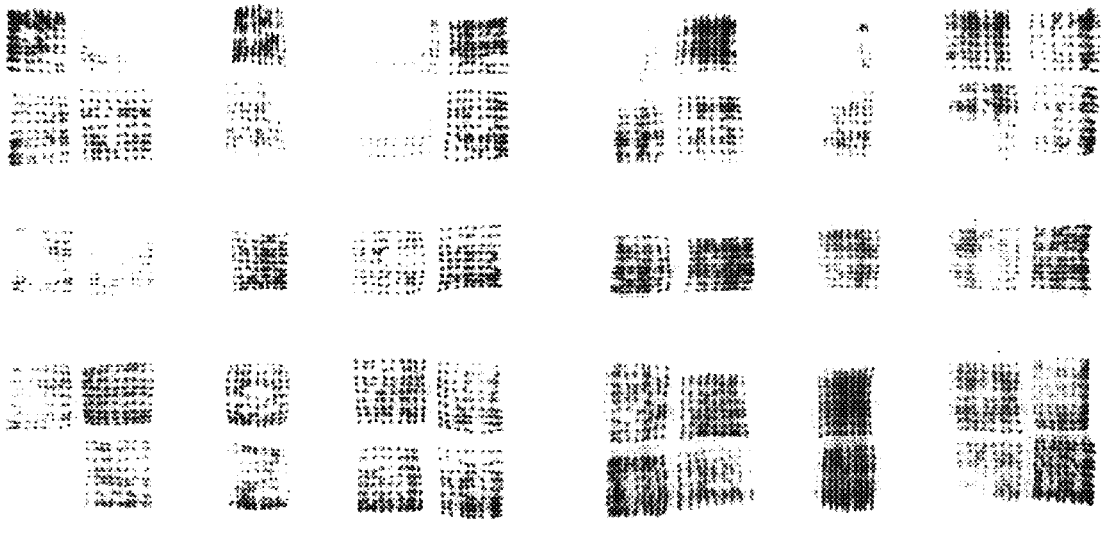
FIGS. 14a–b show the flood histograms of detector plate 1 (FIG. 14a) and 2 (FIG. 14b)

A flood source histogram image was obtained separately for each plate. (FIGS. 14a and b). A 2 cm diameter $^{68}$Ge disc source was used to irradiate each plate independently. The 8 position signals (4X and 4Y) coming from the readout board were integrated for about 0.2 microseconds and fed into the analog-to-digital conversion (ADC) board located inside the data acquisition computer. The lower energy threshold was set to about 100 keV with the aid of the constant fraction discriminator and no upper threshold was applied. After collecting the list mode data from an experiment, the X and Y coordinates were calculated on an event by event basis from the 8 digitized position signals using the modified Anger logic scheme described previously. The X and Y coordinates were then histogrammed to create a 2-D position map. This process was performed for each plate independently.

Results

A flood image of one of the detector plates 22 is shown in FIG. 14a. More than 95% of the 2025 crystals were identified on each detector plate. The variations in the intensity of the different crystal elements was due to differences in gain, coupling variations, differences in the LSO light output and variations in the amount of reflector in between the crystals. The flood images appeared to be segmented into 9 separate sectors because of the multiplexed sector readout scheme. The uniform background in the flood image was probably a combination of noise due to the low threshold and contributions from inter-crystal scatter.

C. Position Look-Up Tables and Energy Resolution

Boundaries were drawn on the 2-D histogram maps obtained from the examples above and were used to generate look-up-tables (LUTs) for each sector for both the detector plates 22. The LUT was then used to relate the position in the 2-D histogram to the appropriate crystal element in the LSO array. In order to generate an energy histogram plot for each element, the list mode data were then resorted based on the total pulse amplitudes (sum of the 4 position signals) for a particular crystal. These energy spectra were then analyzed to determine the FWHM which provided a measure of the energy resolution.

Results

The average energy resolution for each detector plate was calculated as the average of the energy resolutions for the individual crystal elements for which the photopeak could be identified. The average energy resolution for detector plate 1 was about 22.9%, with a range of 14–39%. The average energy resolution for detector plate 2 was about 20.4%, with a range of about 12–28%. Greater than 90% of the crystals had clear photopeaks from which the energy resolution was determined and included in the averages quoted above.

D. Timing Resolution

The two detector plates 22 were connected in coincidence. A $^{22}$Na point source 14 was placed at the center of the two detector plates 22. The singles rates on each detector were kept low by using a weak source to minimize random events. For each detected coincidence event, the sum of the 8 position signals from each detector plate was sent to constant fraction discriminators which generated the timing pulses. These two timing pulses, one for each detector plate, were in turn fed into a calibrated time-to-amplitude converter (TAC) module. The output from the TAC was then digitized to produce the timing spectrum. A background measurement, acquired for the same amount of time, was taken without the source and subtracted to remove coincidences due to LSO background.

Results

Figure 15:
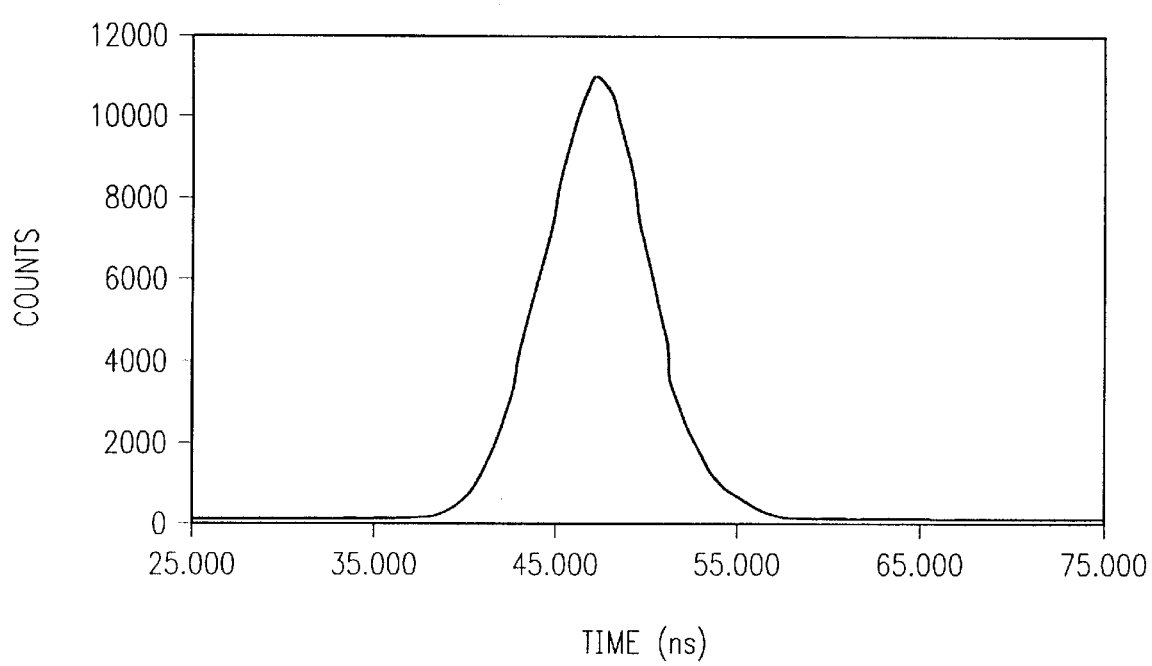
FIG. 15 shows the coincidence timing spectrum of two detector plates, indicating a FWHM of 8.1 ns.

The timing spectrum measured with a positron source placed at the center of the two detector plates 22 is shown in FIG. 15. The FWHM of the time response was 8.1 ns. This was a different response than that measured with the two single detector modules 20 alone, which showed a 2.4 ns timing resolution. This result may be due to lack of time alignment of the 50 detector modules as well as variable, position dependent delays introduced in the readout board itself. Thus, a timing window of 16–20 ns could be beneficial.

E. Phantom Image

An acrylic line source phantom of size 4.78×1.08×13 cm consisting of 8 drilled channels was filled with FDG and imaged. Each square channel measured 1.08×1.08×130 mm producing a fillable volume of 0.15 ml. The channels were spaced with a variable center-to-center distance as follows: 10 mm, 8.5 mm, 7 mm, 5.5 mm, 4 mm, 2.5 mm and 1 mm. The total amount of activity in the phantom was approximately 50 µCi. The phantom was imaged for approximately 1½ minutes for a total of 1.1 million coincidence counts at an average count rate of 10,500 counts per second. No corrections were made for random coincidences or individual detector efficiencies. An energy threshold of about 250 keV was applied to the data.

Results

Figure 16A:
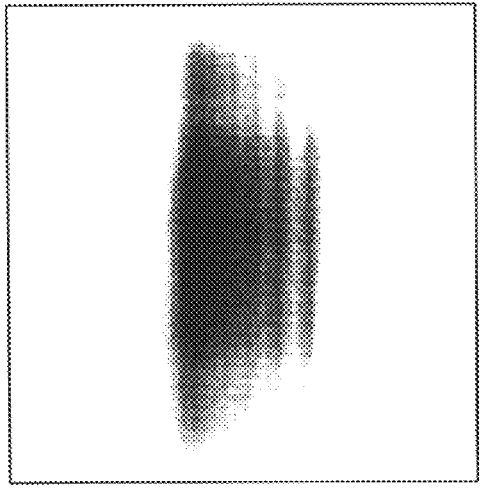
FIGS. 16a–b are images of the line bar phantom reconstructed using the focal plane tomography algorithm, FIG.
Figure 16B:
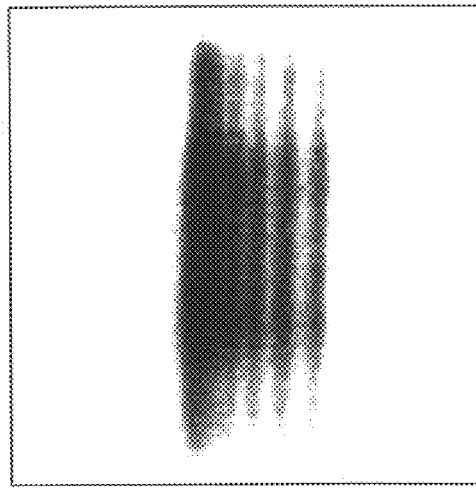

A line bar phantom was scanned with the system comprising the two 15×15 cm$^2$ planar scintillation detector plates 22, and the images were reconstructed using focal plane tomography. The images from the line bar phantom experiments are shown in FIGS. 16a and b and represent the in-focus plane. FIG. 16a was reconstructed using a full angle of acceptance of +/−45° where each detector element may be in coincidence with every other detector element in the opposing plate. The image contains 1.1 million events. FIG. 16b was reconstructed using a half angle of acceptance of +/−22.5° and contained 550,000 events. Each image was scaled to the maximum value in the respective image. No corrections were applied to either Figure.

F. Projection Image Resolution

Images were generated using a simple focal plane tomography algorithm (simple backprojection). Two sets of images were reconstructed, one using line of responses (LORs) corresponding to the full angle of acceptance (+/−45°) and the other using LOR's from one half of the full acceptance angle (+/−22.5°). Profiles through the line bar images were taken and analyzed to assess the point at which two adjacent channels were no longer distinguishable as two separate lines.

Results

Figure 17A:
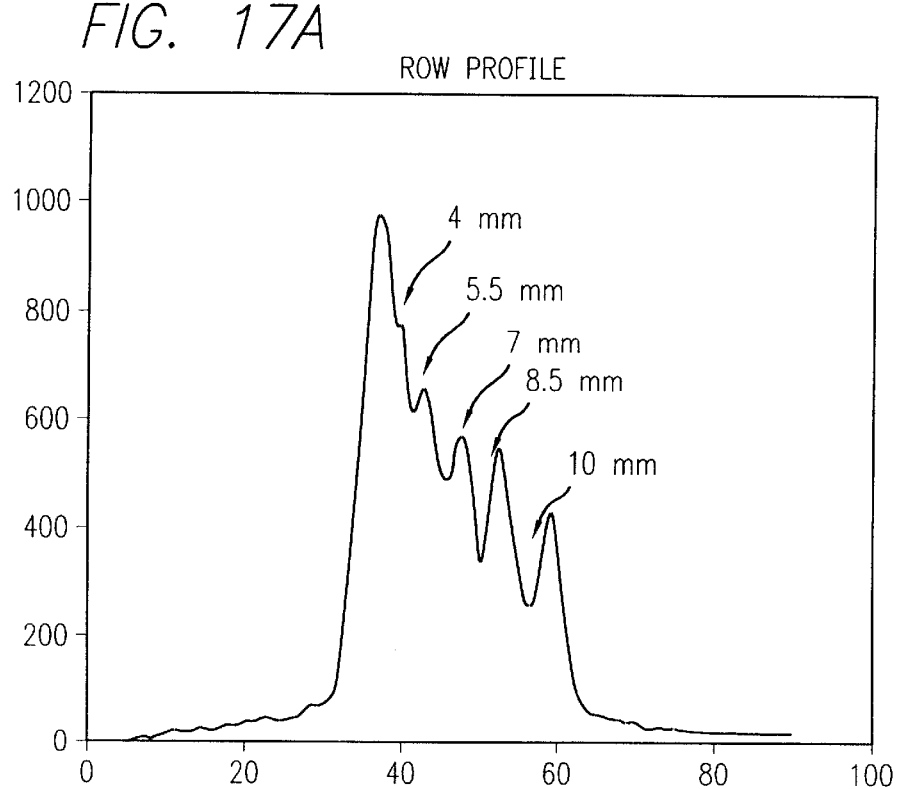
FIGS. 17a–b are row profiles taken through the line bar phantom images.
Figure 17B:
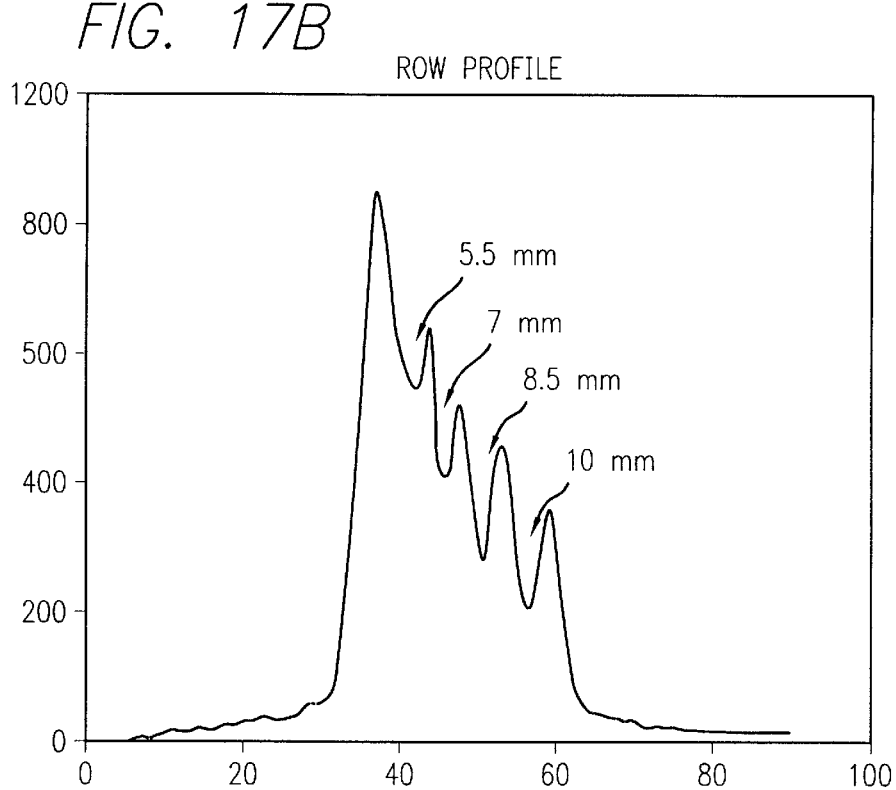

Qualitatively, one is able to visually separate the first three lines in the FIG. 16a and the first four lines in FIG. 16b. Profiles taken through the two images are shown in FIGS. 17a and b. In the profile obtained from the FIG. 16a (full angle of acceptance), six clear peaks may be identified. The distance between the two closest peaks represents a physical distance of 4 mm. In the profile obtained from FIG. 16b (half angle of acceptance), five peaks may be clearly identified. The distance between the two closest peaks in this profile represents 5.5 mm. The differences in the images in this experiment are minimal as seen in the profiles.

IV. Discussion and Conclusions

In the flood images, greater than 95% of the crystals were identified and look-up tables were created. The energy resolution was measured to be an average of about 21.6% across both plates 22, which is within the expected range. The timing resolution was measured to be 8.1 ns for the entire system. Phantom images of a line bar phantom provided an initial estimate of the projection image resolution of the system using the focal plane tomography algorithm. Two lines separated by a distance of 4 mm were visualized in the phantom image without any corrections.

The following references are incorporated herein by reference: U.S. Provisional Application No. 60/170,746; American Cancer Society, "Cancer Facts and Figures—

1998," American Cancer Society, Atlanta, Ga. 1998; M. Moskovitz, Cancer, 51,1007–1011 (1983); K. Kerlikowske, et al., J. Natl. Can. Inst., 90, 1801–1809 (1998); O. Warburg, Science, 123, 309–314 (1956); C. K. Hoh, et al., Sem. Nucl. Med., 27, 94–106 (1997); N. Y. Tse, et al., Ann Surg., 216, 27–34 (1992); O. E. Nieweg, et al., Ann. N. Y. A. Sci., 698, 423–448 (1993); R. L. Wahl, et al., Radiology, 179, 765–770 (1991); N. Avril, et al., J Clin. Onc., 14, 1848–1857 (1996); L. Adler, et al., Radiology, 203, 323–327 (1997); C. J. Thompson, et al., IEEE Trans. Nucl. Sci., 42,1012–1017 (1995); C. J. Thompson, et al., Med. Phys., 21, 529–537 (1994); J. L. Robar, et al., Nucl. Instrum. Methods Phys. Res. A, 392, 402–406 (1997); I. Weinberg, et al., Eur. J. Nucl. Med., 23, 804–806 (1996); R. Freifelder, et al., Phys. Med. Biol., 42, 2463–2480 (1997); G. Hutchins, et al., J. Nucl. Med., 36, 69P (1995); W. Moses, et al., J. Nucl. Med., 36, 69P (1995); A. A Bergman, et al., Med. Phys., 25, 2119–2129 (1998); M. B. Williams, et al., Proc. Int. Soc. Opt. Eng., 3115, 226–234 (1997); M E. Casey, et al., IEEE Trans. Nucl. Sci., 33, 460–463 (1986); S. R. Cherry, et al., IEEE Trans. Nucl. Sci., 42,1064–1068 (1995); J. J. Vaquero, et al., IEEE Trans. Nucl. Sci., 17, 967–978 (1998); R. Pani, et al., IEEE Trans. Nucl. Sci., 46, 702708(1998); R. Slates, et al., IEEE Trans. Nucl. Sci., 47, 1018–1023 (2000); J. S. Huber, et al., Nucl. Inst. Meth., 437, 374–380 (1999); K. Kurashige, et al., IEEE Trans. Nucl. Sci., 45, 522–524 (1998); W. Budde, J. Opt. Soc. Am., 50, 217–220 (1960); S. R. Cherry, et al., IEEE Trans. Nucl. Sci., 43,1932–1937 (1996); E. Peli, et al., J. Opt. Soc. Amer. A, 12, 2274–2285 (1995); H. Anger, Rev. Sci. Instr., 29, 27–33 (1958).

Although the foregoing invention has been described in some detail by way of illustration and example for purposes of clarity and understanding, it will be obvious that various modifications and changes which are within the knowledge of those skilled in the art are considered to fall within the scope of the invention.

What is claimed is:

1. A positron emission tomography imaging apparatus comprising:

at least two, opposed detectors, said detectors having an array of scintillation crystals, a plurality of position-sensitive photomultiplier tubes positioned adjacent said plurality of arrays, and a lightguide having an end positioned adjacent to said array of scintillation crystals and having an opposing end adjacent to said photomultiplier tubes.

2. The apparatus of claim 1, wherein each array comprises at least nine crystals.

3. The apparatus of claim 1, wherein said crystals are lutetium oxyorthosilicate (LSO) or light-output equivalent crystals.

4. A PET imaging apparatus comprising:

at least two detector plates, each plate comprised of at least one detector, said detector having a scintillator coupled to one end of a lightguide, the opposing end of said lightguide coupled to a position-sensitive photomultiplier tube.

5. The apparatus of claim 4 wherein said scintillator comprising an array of lutetium oxyorthosilicate (LSO) scintillator crystals.

6. The apparatus of claim 4 wherein said lightguide is an optical fiber bundle.

7. A method for examining a body part comprising:

providing an internal image of the body part including, a positron emitting radioisotope and a positron recording apparatus between which the body part is to be disposed; and placing at least two detector plates over different areas of the body part, each plate comprised of at least one detector, said detector having a scintillator coupled to one end of a lightguide, the opposing end of said lightguide coupled to a photomultiplier tube, said detector is capable of detecting gamma-rays emitted by the radioisotope infiltrated into the body part in an adjacent relationship with said recording apparatus for providing the internal image.

8. The method of claim 7, wherein said scintillator comprises an array of lutetium oxyorthosilicate (LSO) scintillator crystals or light-output equivalent crystals.

9. The method of claim 7, wherein said lightguide is an optical fiber bundle.

* * * * *